(12) United States Patent
Seaton

(10) Patent No.: US 7,264,258 B1
(45) Date of Patent: Sep. 4, 2007

(54) LEG ABDUCTOR ASSEMBLY

(76) Inventor: Jason M. Seaton, 2117 Andy Holt Ave., Knoxville, TN (US) 37916

( * ) Notice: Subject to any disclaimer, the term of this patent is extended or adjusted under 35 U.S.C. 154(b) by 36 days.

(21) Appl. No.: 11/144,218

(22) Filed: Jun. 6, 2005

(51) Int. Cl.
*A61G 5/10* (2006.01)

(52) U.S. Cl. .................... 280/304.1; 280/8.4; 224/401; 224/407; 224/275; 224/550

(58) Field of Classification Search ................ 280/8.4, 280/304.1; 224/401, 407, 275, 560
See application file for complete search history.

(56) References Cited

U.S. PATENT DOCUMENTS

| | | | | |
|---|---|---|---|---|
| 2,931,550 A * | 4/1960 | Wood | ........................... | 224/275 |
| 3,338,629 A * | 8/1967 | Drees | ...................... | 312/235.8 |
| 3,526,314 A * | 9/1970 | Trammell, Jr. | .............. | 224/275 |
| 3,614,136 A * | 10/1971 | Dent | .......................... | 280/500 |
| 3,909,092 A * | 9/1975 | Kiernan | .................... | 312/235.8 |
| 4,372,299 A | 2/1983 | Fixel | | |
| 4,392,489 A | 7/1983 | Wagner, Sr. | | |
| 4,403,786 A * | 9/1983 | Ulics | ....................... | 280/304.1 |
| 4,700,634 A | 10/1987 | Mills et al. | | |
| 4,730,869 A | 3/1988 | Schumacher | | |
| 5,181,275 A * | 1/1993 | Spulgis | ........................... | 2/48 |
| 5,207,477 A | 5/1993 | Maxwell | | |
| 5,263,578 A * | 11/1993 | Narvey | ....................... | 206/232 |
| 5,362,305 A | 11/1994 | Varn | | |
| 5,397,160 A | 3/1995 | Landry | | |
| 5,573,288 A | 11/1996 | Raffensperger | | |
| 5,743,452 A * | 4/1998 | Liu | .............................. | 224/275 |
| 5,901,891 A * | 5/1999 | Douglass | ..................... | 224/407 |
| 5,979,987 A * | 11/1999 | Rich | ...................... | 297/411.23 |
| D445,726 S | 7/2001 | Schlangen | | |
| 6,269,992 B1 * | 8/2001 | Miller | ......................... | 224/407 |
| 7,052,023 B2 * | 5/2006 | Chen et al. | .............. | 280/47.38 |

* cited by examiner

*Primary Examiner*—Lesley D. Morris
*Assistant Examiner*—Marlon Arce-Diaz

(57) ABSTRACT

A leg abductor assembly includes a housing that has a bottom wall and a peripheral wall that is attached to and extends upwardly from the bottom wall. The peripheral wall includes a pair of side walls and a pair of end walls. A cover is hingedly coupled to the upper edge for selectively opening or closing the opening. A bracket is attached to the bottom wall. The bracket is configured to removably couple the housing to a front edge of a wheelchair.

8 Claims, 3 Drawing Sheets

LEG ABDUCTOR ASSEMBLY

BACKGROUND OF THE INVENTION

1. Field of the Invention

The present invention relates to abductor devices and more particularly pertains to a new abductor device for abducting the legs of a person positioned in a wheel chair and for also providing a storage and transportation device for small objects.

2. Description of the Prior Art

The use of abductor devices is known in the prior art. U.S. Pat. No. 4,372,299 describes an abductor pillow which is positionable between the legs of a patient and which includes a removable portion for the receiving of a catheter. Another type of abductor device is U.S. Pat. No. 4,392,489 and includes another abductor pillow having a plurality of straps attached thereto for securing the pillow where needed. Yet another such device is found in U.S. Pat. No. 5,362,305 which includes straps attachable to legs and having a rod extending between the straps.

While these devices fulfill their respective, particular objectives and requirements, the need remains for a device that is attachable to a wheelchair for abducting the legs of a person positioned in a wheel chair. Additionally, the device preferably includes an accessible interior which may be used holding and transporting small objects.

SUMMARY OF THE INVENTION

The present invention meets the needs presented above by generally comprising a housing that has a bottom wall and a peripheral wall that is attached to and extends upwardly from the bottom wall. The peripheral wall includes a pair of side walls and a pair of end walls. A cover is hingedly coupled to the upper edge for selectively opening or closing the opening. A bracket is attached to the bottom wall. The bracket is configured to removably couple the housing to a front edge of a wheelchair.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
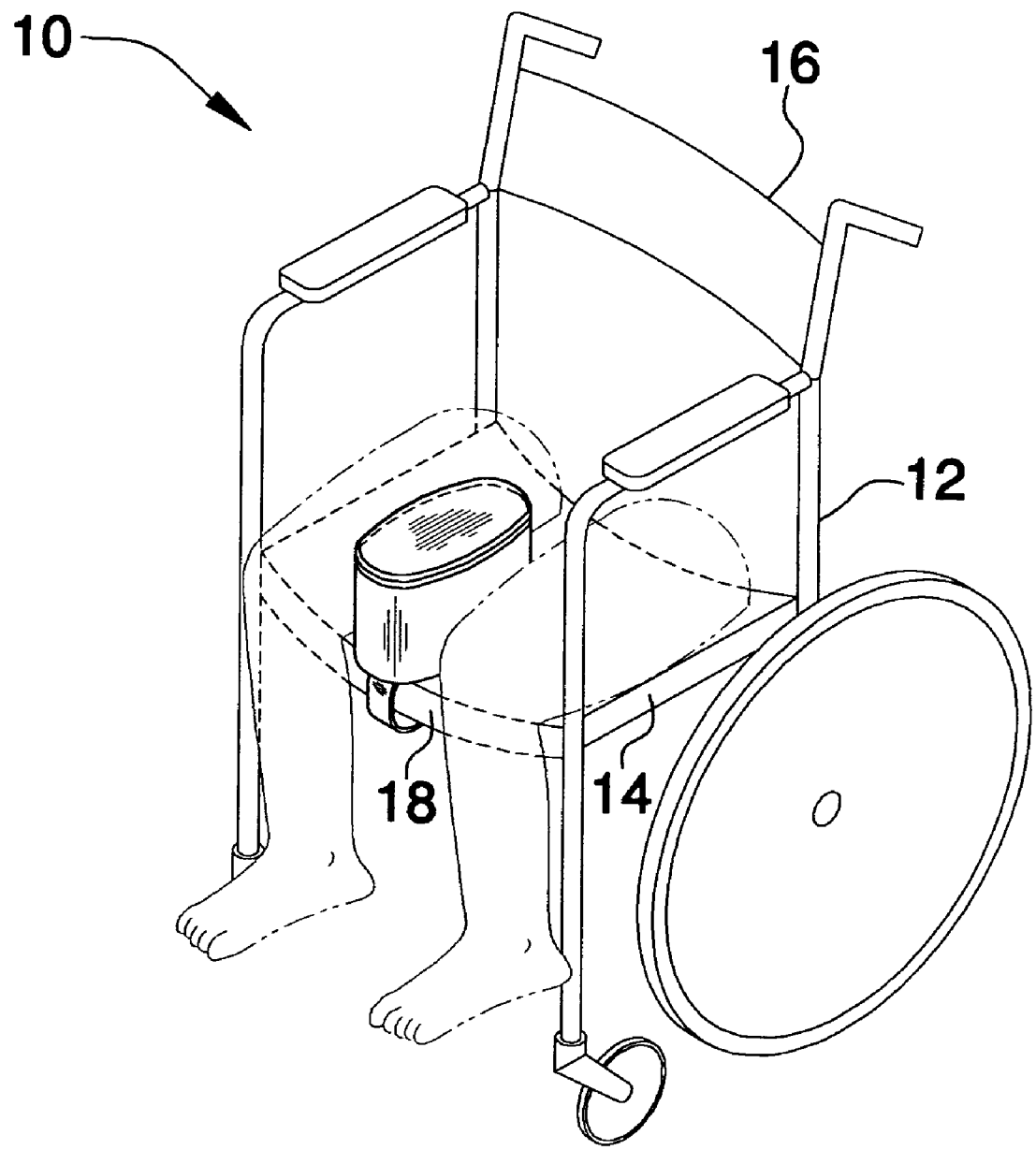
FIG. 1 is a perspective in-use view of a leg abductor assembly according to the present invention.
Figure 2:
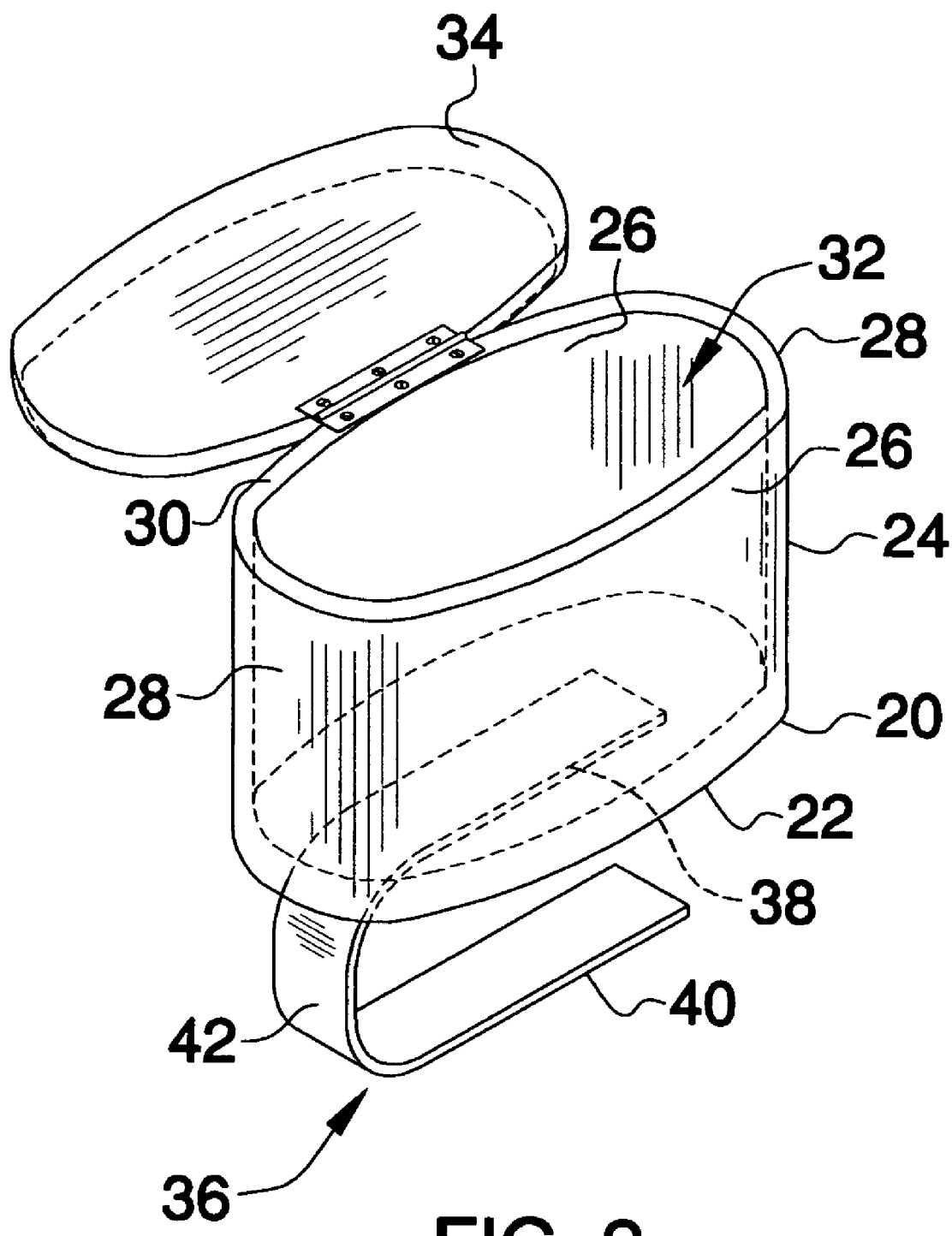
FIG. 2 is a top perspective view of the present invention.
Figure 3:
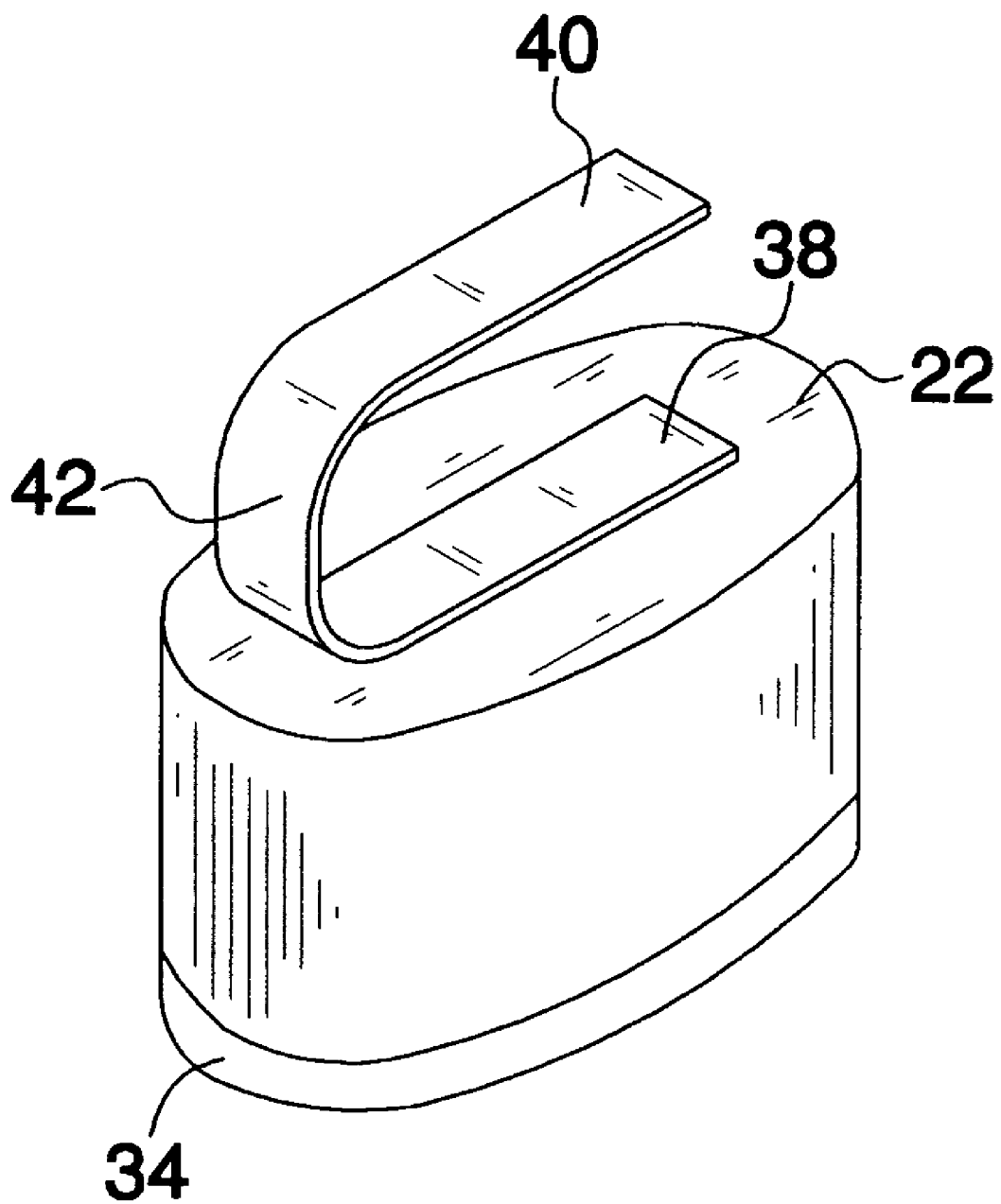
FIG. 3 is a bottom perspective view of the present invention.

With reference now to the drawings, and in particular to FIGS. 1 through 3 thereof, a new abductor device embodying the principles and concepts of the present invention and generally designated by the reference numeral 10 will be described.

As best illustrated in FIGS. 1 through 3, the leg abductor assembly 10 generally comprises a wheelchair 12 that includes a seat portion 14 and a backrest portion 16. The seat portion 14 has a front edge 18.

A housing 20 has a bottom wall 22 and a peripheral wall 24 that is attached to and extends upwardly from the bottom wall 22. The peripheral 24 wall includes a pair of side walls 26 and a pair of end walls 28. Each of the end walls 28 is arcuate and extends outwardly away from each other. The peripheral wall 24 has an upper edge 30 that defines an opening 32 extending into the housing 20. A cover 34 is hingedly coupled to the upper edge 30 for selectively opening or closing the opening 32.

A bracket 36 is attached to the bottom wall 22. The bracket 36 is configured to removably couple the housing 20 to the front edge 18 of the wheelchair 12. The bracket 36 includes a first arm 38, a second arm 40 and a middle section 42 attached to and extending between the first 38 and second 40 arms. The arms 38, 40 are orientated generally parallel with respect to each other. The first arm 38 is attached to the bottom wall 22 and is orientated parallel to a line orientated parallel to planes of the side walls 26. The seat portion 14 is extendable between the first 38 and second 40 arms.

In use, the housing 20 acts as a leg abductor for a person seated in the wheelchair 12. The housing 20 additionally allows a person to store and transport small objects in a manner that allows those objects to be easily accessible.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A leg abduction and container combination assembly comprising:
    a wheelchair;
    a housing having a bottom wall and a peripheral wall being attached to and extending upwardly from said bottom wall, said peripheral wall including a pair of side walls and a pair of end walls;
    a cover being hingedly coupled to said upper edge for selectively opening or closing said opening; and
    a bracket being attached to said bottom wall, said bracket being configured to removably couple said housing to a front edge of a seat rest of a wheelchair and positioning said housing between legs of a person seated in the wheelchair.

2. The assembly according to claim 1, wherein each of said end walls are arcuate and extend outwardly away from each other.

3. The assembly according to claim 1, wherein said bracket includes a first arm, a second arm and a middle section attached to and extending between said first and second arms, said arms being orientated generally parallel with respect to each other, said first arm being attached to said bottom wall and being orientated parallel to a line orientated parallel to planes of said side walls.

4. A leg abduction and container combination assembly comprising:
   a wheelchair;
   a wheelchair including a seat portion and a backrest portion, said seat portion having a front edge;
   a housing having a bottom wall and a peripheral wall being attached to and extending upwardly from said bottom wall, said peripheral wall including a pair of side walls and a pair of end walls, each of said end walls being arcuate and extending outwardly away from each other, said peripheral wall having an upper edge defining an opening extending into said housing;
   a cover being hingedly coupled to said upper edge for selectively opening or closing said opening; and
   a bracket being attached to said bottom wall, said bracket being configured to removably couple said housing to said front edge of a seat rest of said wheelchair and positioning said housing between legs of a person seated in the wheelchair, said bracket including a first arm, a second arm and a middle section attached to and extending between said first and second arms, said arms being orientated generally parallel with respect to each other, said first arm being attached to said bottom wall and being orientated parallel to a line orientated parallel to planes of said side walls, said seat portion being extendable between said first and second arms.

5. A method of abducting legs of a person comprising the steps of:
   providing a wheelchair;
   providing a housing having a bottom wall and a peripheral wall being attached to and extending upwardly from said bottom wall, said peripheral wall including a pair of side walls and a pair of end walls;
   providing a cover being hingedly coupled to said upper edge for selectively opening or closing said opening;
   providing a bracket being attached to said bottom wall, said bracket being configured to removably couple said housing to a front edge of a wheelchair; and
   attaching said housing to the front edge of a seat rest of the wheelchair and between the legs of the person while the person is seated in the wheelchair.

6. The method according to claim 5, wherein the step of providing a housing includes the step of each of said end walls being arcuate and extend outwardly away from each other.

7. The method according to claim 6, wherein the step of providing said bracket includes the step of said bracket including a first arm, a second arm and a middle section attached to and extending between said first and second arms, said arms being orientated generally parallel with respect to each other, said first arm being attached to said bottom wall and being orientated parallel to a line orientated parallel to planes of said side walls.

8. The method according to claim 5, wherein the step of providing said bracket includes the step of said bracket including a first arm, a second arm and a middle section attached to and extending between said first and second arms, said arms being orientated generally parallel with respect to each other, said first arm being attached to said bottom wall and being orientated parallel to a line orientated parallel to planes of said side walls.

* * * * *